US012636443B2

(12) United States Patent
Korolik et al.

(10) Patent No.: US 12,636,443 B2
(45) Date of Patent: May 26, 2026

(54) INJECTION SYRINGE

(71) Applicant: AH2I MEDICAL GROUP, Ramat-Gan (IL)

(72) Inventors: Pavel Korolik, Petah Tiqva (IL); Alexander Liberzon, Netanya (IL); Inna Kogan, Petah Tiqva (IL)

(73) Assignee: AH2I MEDICAL GROUP, Ramat-Gan (IL)

( * ) Notice: Subject to any disclaimer, the term of this patent is extended or adjusted under 35 U.S.C. 154(b) by 862 days.

(21) Appl. No.: 17/918,812

(22) PCT Filed: Apr. 15, 2021

(86) PCT No.: PCT/FR2021/050664
§ 371 (c)(1),
(2) Date: Oct. 13, 2022

(87) PCT Pub. No.: WO2021/209721
PCT Pub. Date: Oct. 21, 2021

(65) Prior Publication Data
US 2023/0347073 A1 Nov. 2, 2023

(30) Foreign Application Priority Data
Apr. 15, 2020 (FR) ...................................... 2003755

(51) Int. Cl.
*A61M 5/36* (2006.01)
*A61M 5/31* (2006.01)
*A61M 5/34* (2006.01)

(52) U.S. Cl.
CPC ............ *A61M 5/36* (2013.01); *A61M 5/3129* (2013.01); *A61M 5/34* (2013.01)

(58) Field of Classification Search
CPC ........ A61M 5/36; A61M 5/3129; A61M 5/34; A61M 39/22; A61M 5/20; A61M 5/2066;
(Continued)

(56) References Cited

U.S. PATENT DOCUMENTS

| | | | | |
|---|---|---|---|---|
| 4,610,666 A | * | 9/1986 | Pizzino | A61M 5/19 604/249 |
| 2008/0167621 A1 | * | 7/2008 | Wagner | A61M 5/19 600/432 |

(Continued)

FOREIGN PATENT DOCUMENTS

| CN | 109862928 A | 6/2019 |
|---|---|---|
| WO | WO 2012/139035 A1 | 10/2012 |

(Continued)

OTHER PUBLICATIONS

International Search Report as issued in International Patent Application No. PCT/FR2021/050664, dated Aug. 9, 2021.

*Primary Examiner* — Lauren P Farrar
(74) *Attorney, Agent, or Firm* — CUSHMAN PARTNERS, LLC

(57) ABSTRACT

An injection syringe for injecting a first injectable product into a body injection site of an individual, includes a first barrel containing a first product, a first syringe barrel containing the first injectable product, a first plunger displaceably mounted in the first syringe barrel; a hollow needle to be inserted into the body injection site; an adapter connected to the first syringe barrel and the needle, and a verification device to ensure that, when the first injectable product is injected, the hollow needle is not introduced into a blood vessel. The verification device includes a second syringe barrel containing a second product and connected to the adapter and a second plunger displaceably mounted in the second syringe barrel to cause a depression at the distal end of the hollow needle.

11 Claims, 14 Drawing Sheets

(58) Field of Classification Search
CPC .......... A61M 39/24; A61M 2005/3128; A61M 2039/2433; A61M 2039/244; A61M 2205/50; A61M 2230/20; A61M 2230/201; A61M 5/19; A61M 5/3158; A61M 5/345; A61M 5/142
See application file for complete search history.

(56) References Cited

U.S. PATENT DOCUMENTS

2009/0177158 A1* 7/2009 Krumme ........... A61M 5/14526
604/143
2010/0298811 A1* 11/2010 Connair ................ A61M 5/002
604/82
2011/0118659 A1* 5/2011 Maaskamp ............. A61M 5/19
604/28
2015/0112248 A1 4/2015 Helliwell et al.
2017/0304553 A1* 10/2017 Bender ................... A61M 5/31

FOREIGN PATENT DOCUMENTS

WO      WO 2017/120358  A1      7/2017
WO      WO 2019/243853  A1      12/2019

* cited by examiner

[Fig. 1]
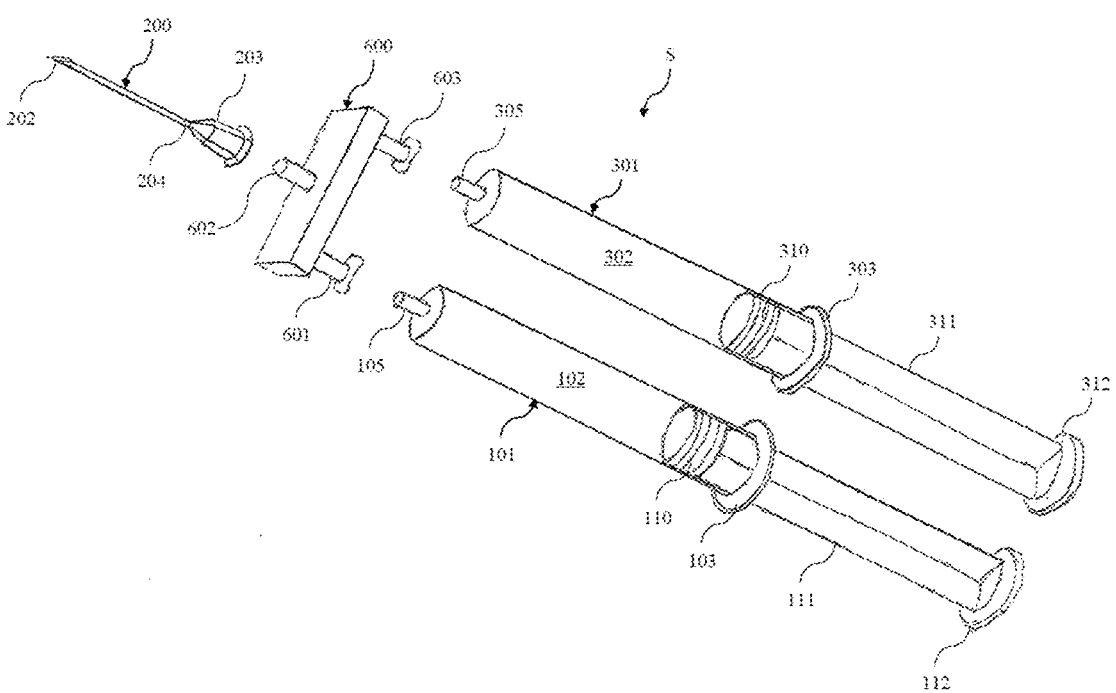

[Fig. 2]
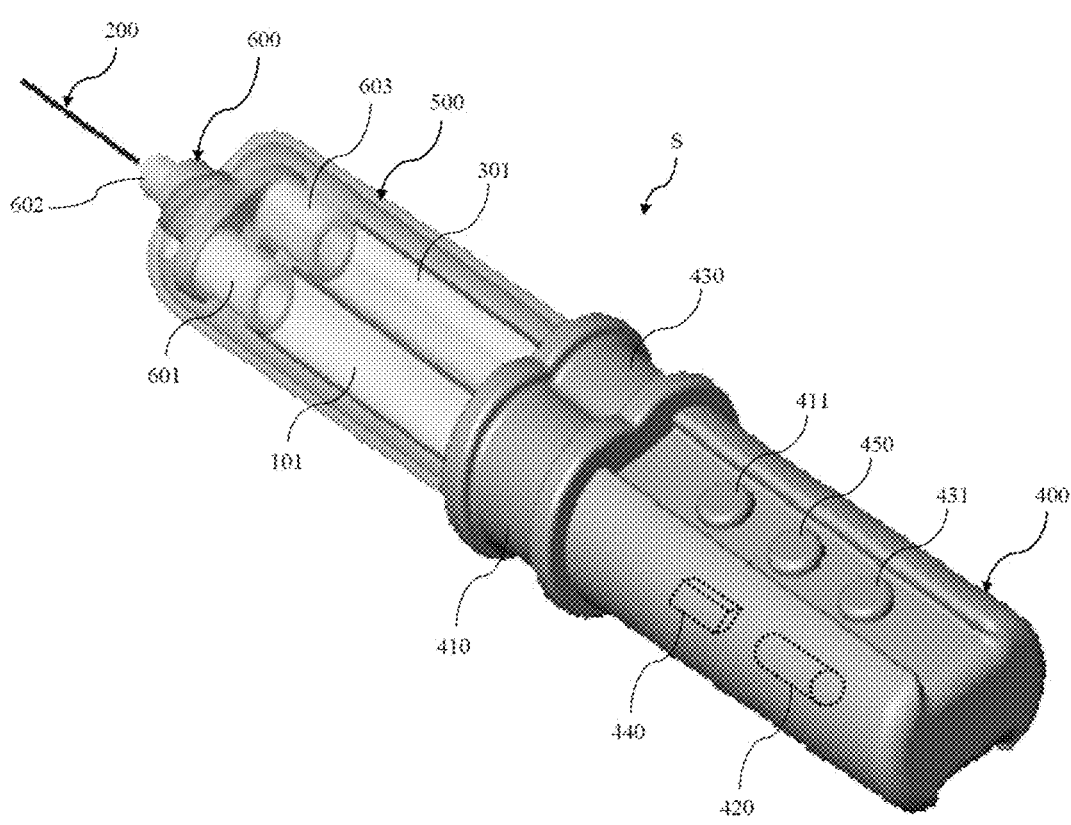

[Fig.3]
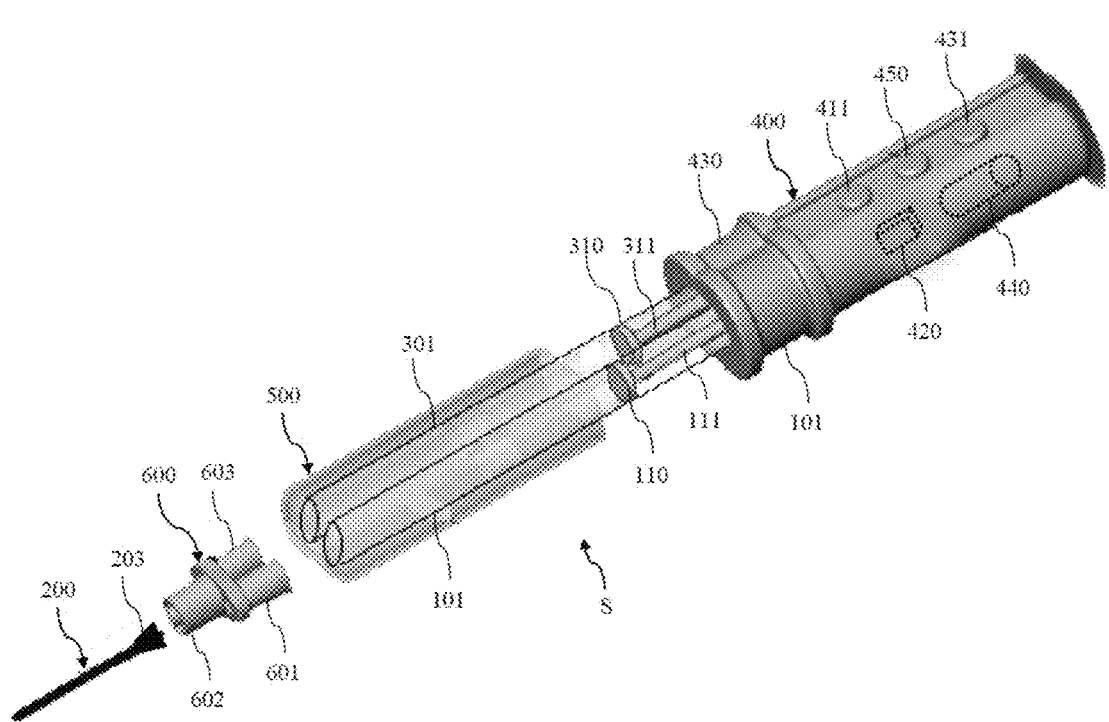

[Fig.4a]
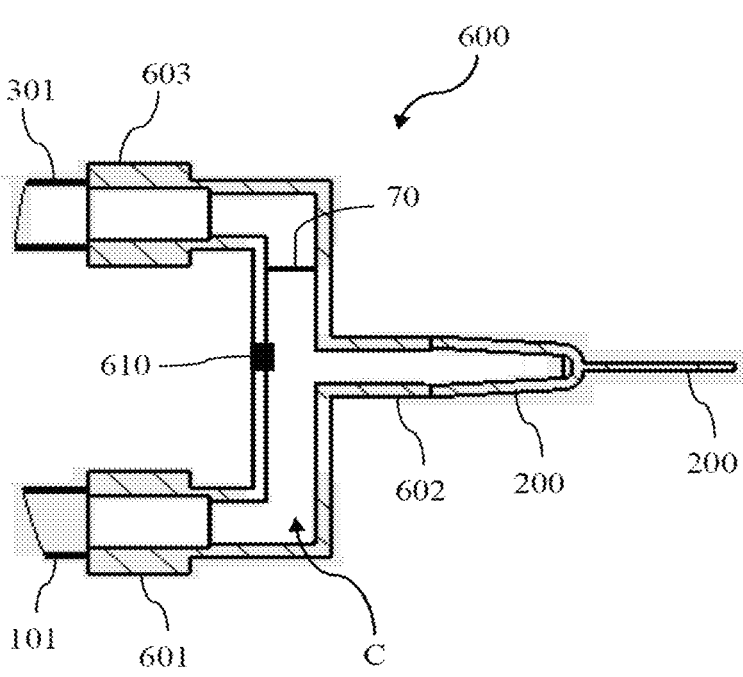
[Fig. 4b]
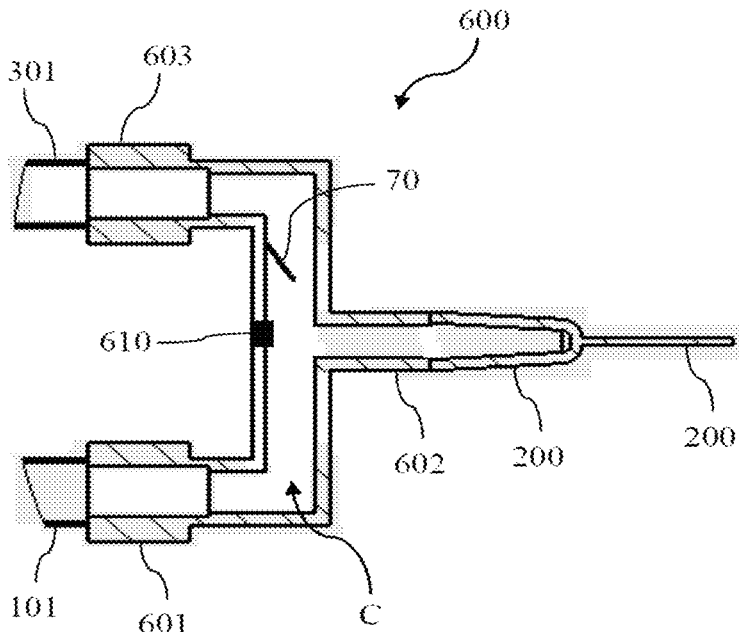

[Fig. 5a]
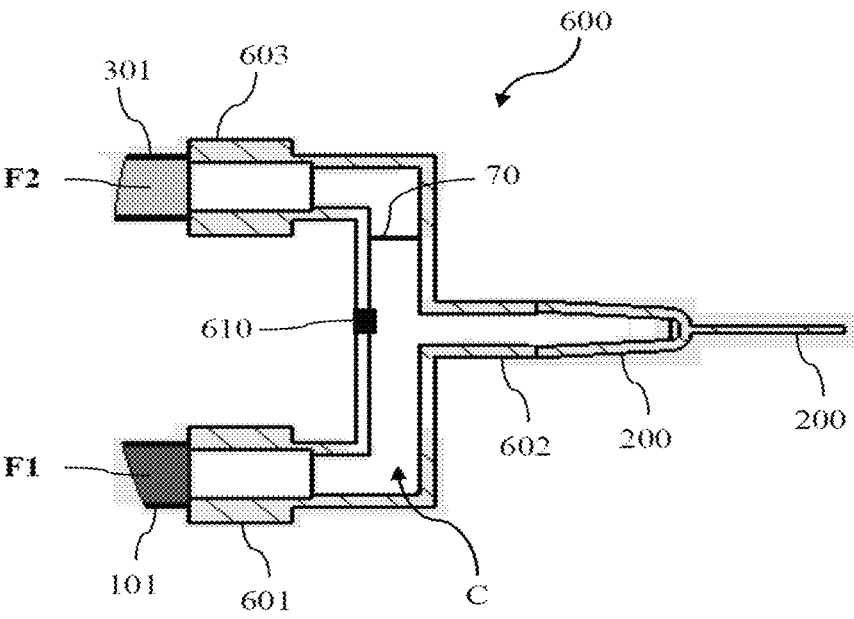
[Fig. 5b]
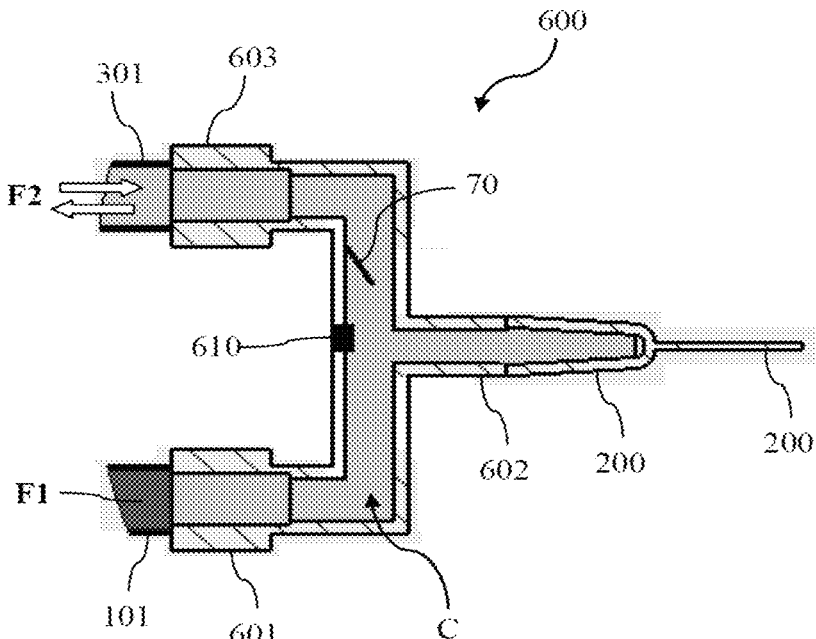

[Fig. 5c]
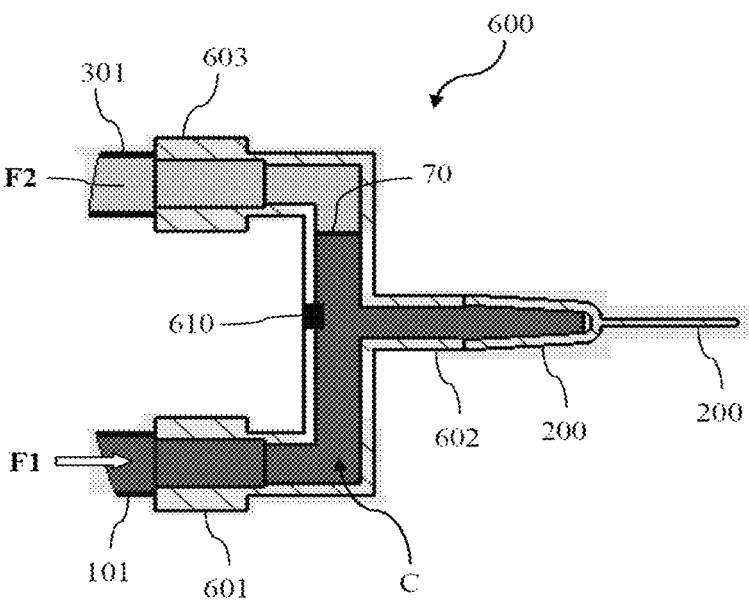
[Fig. 5d]
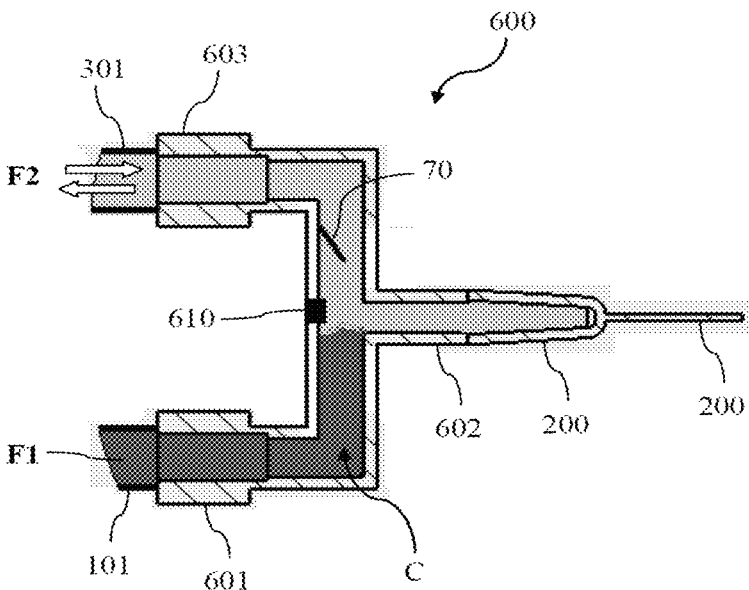

[Fig. 6a]
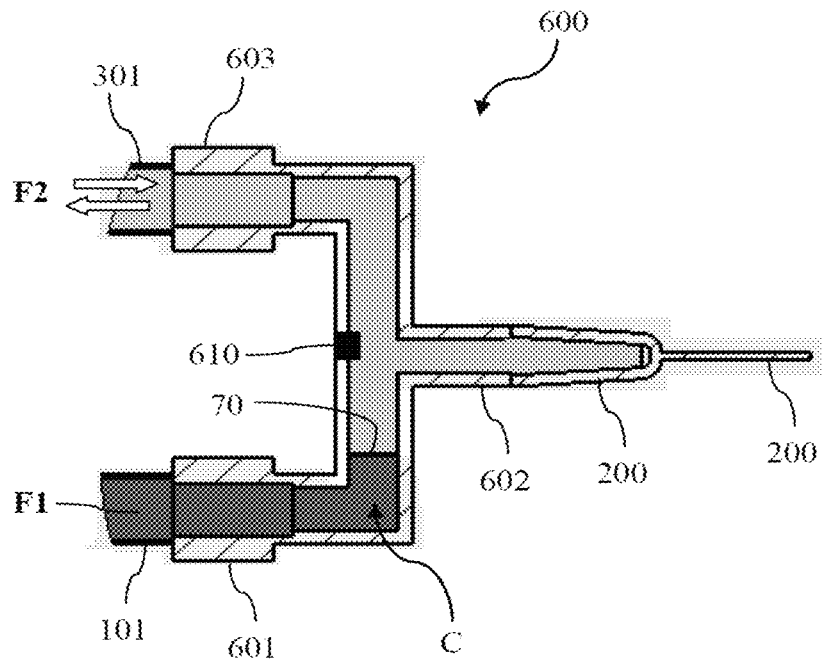
[Fig. 6b]
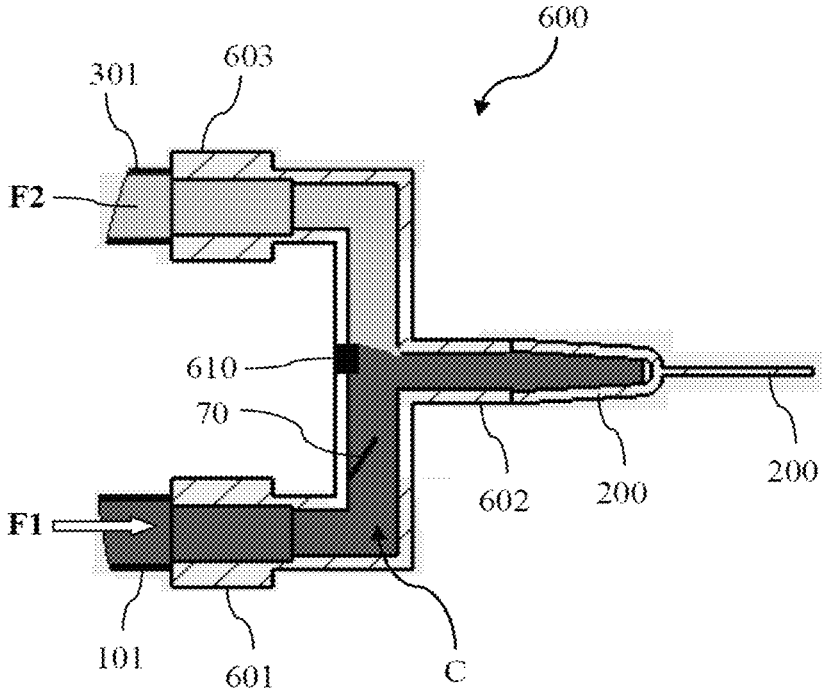

[Fig. 7a]
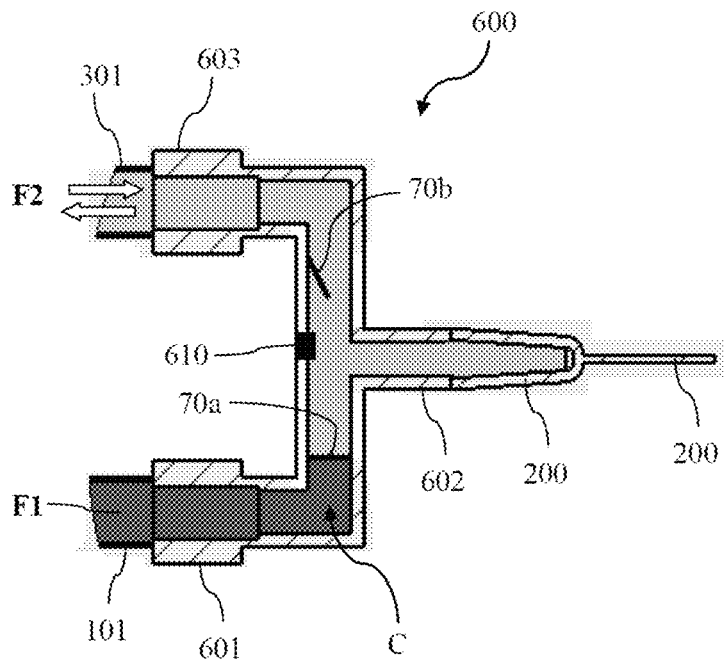
[Fig. 7b]
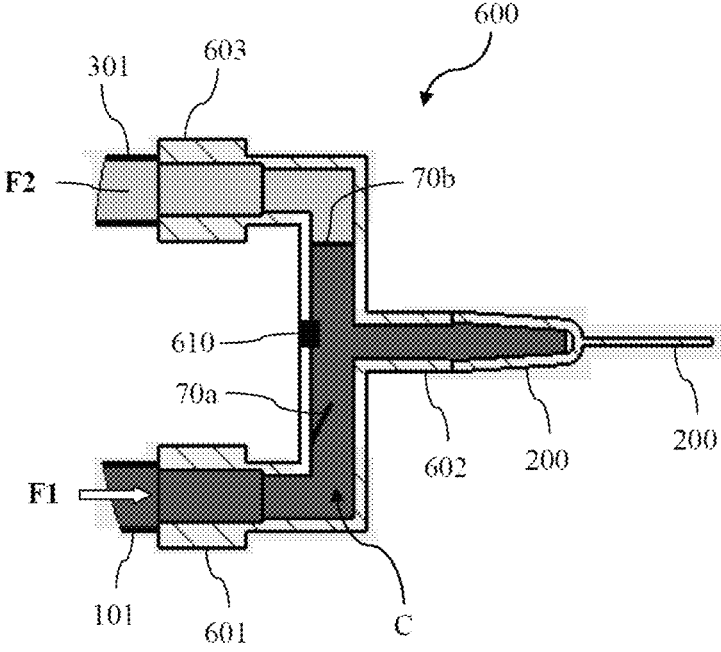

[Fig. 8a]
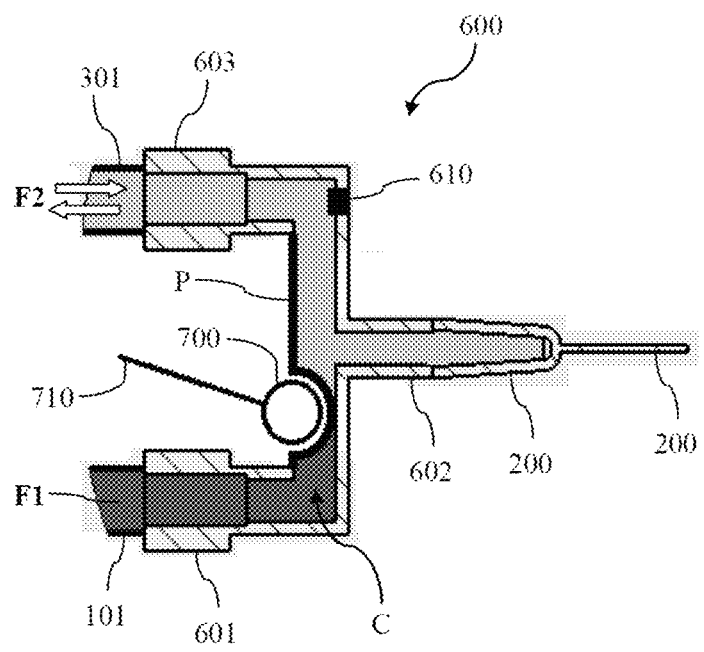
[Fig. 8b]
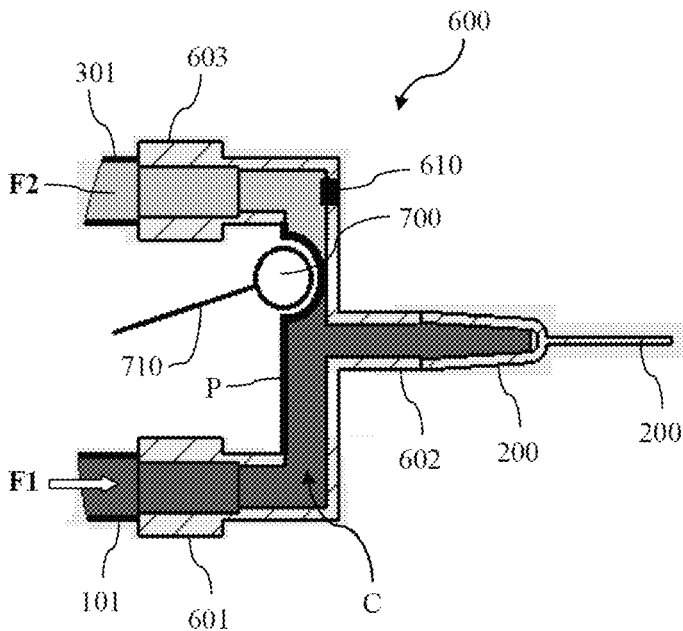

[Fig. 9a]
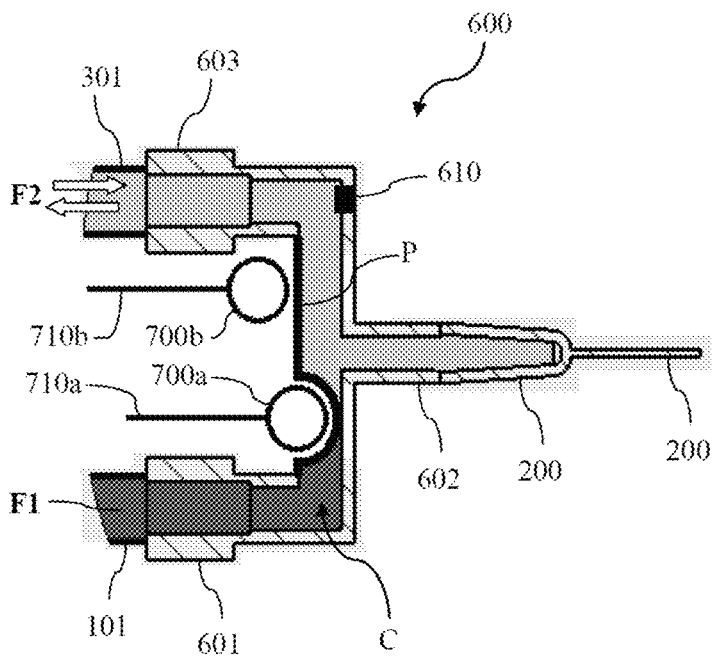
[Fig. 9b]
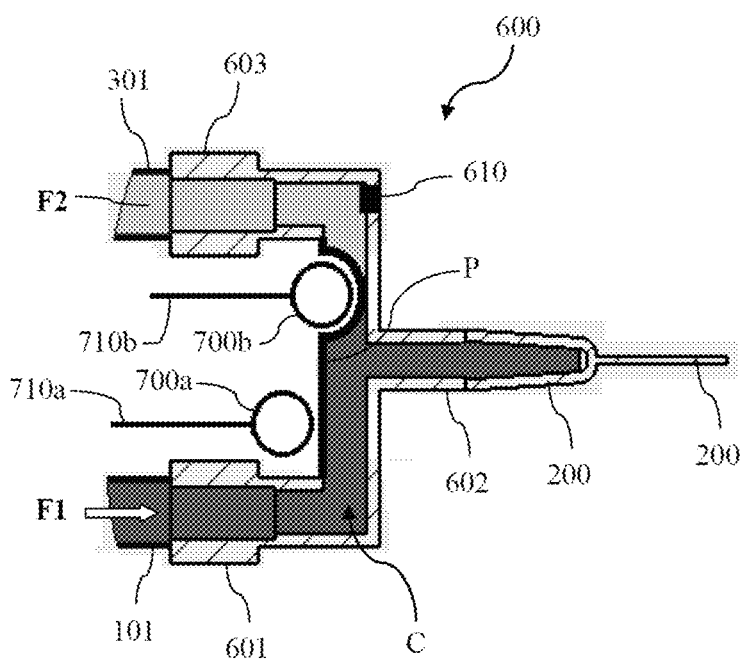

[Fig. 10a]
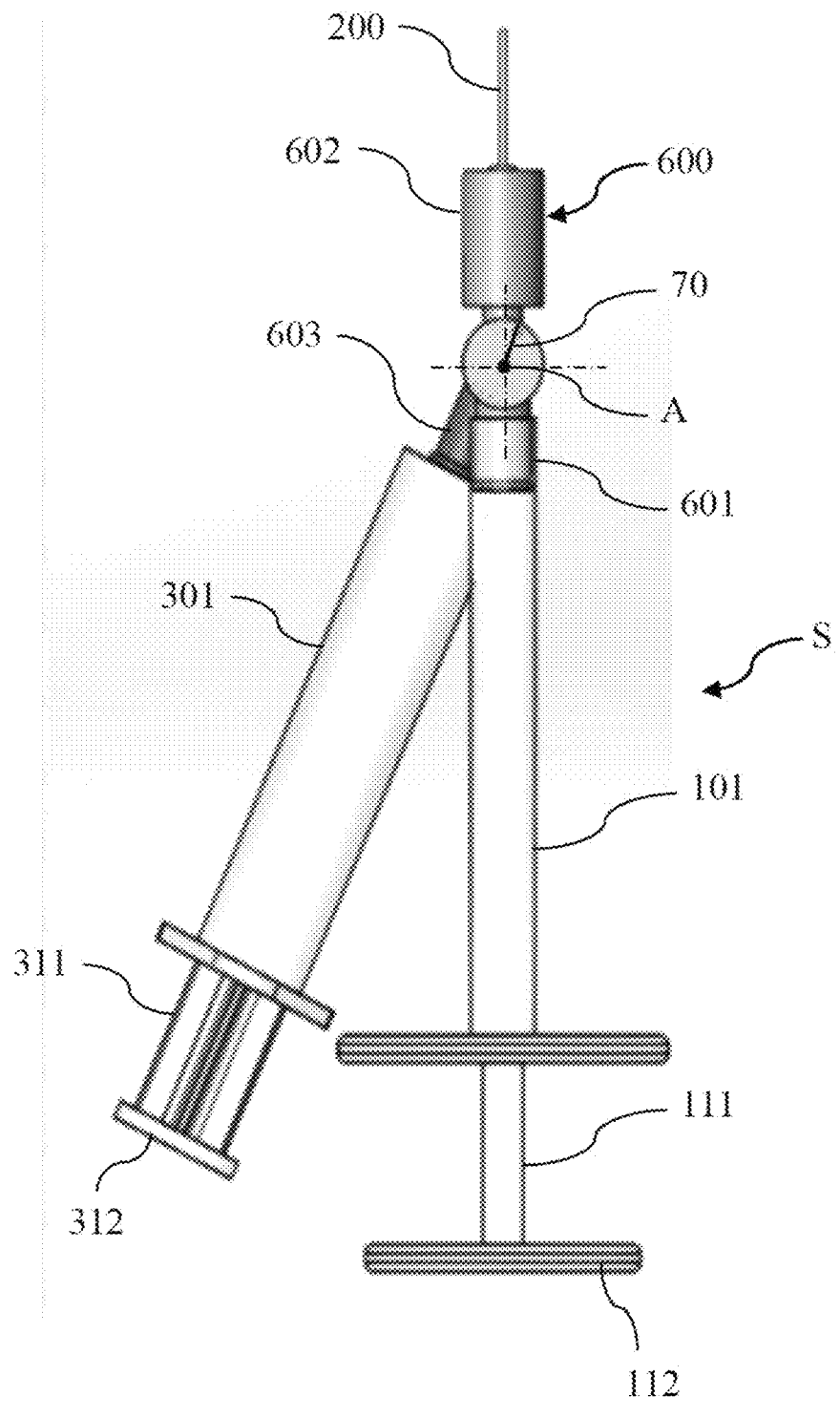

[Fig. 10b]
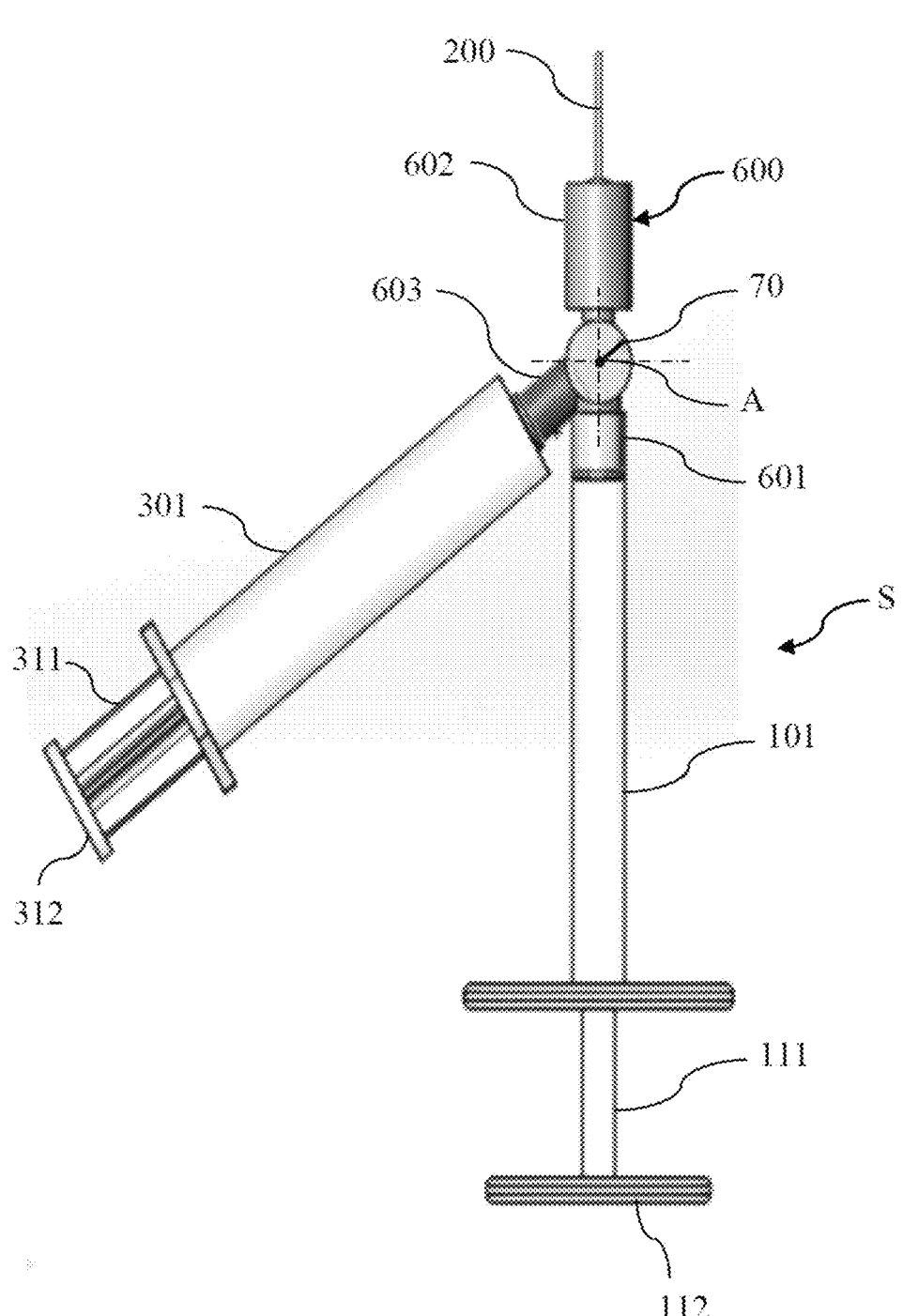

[Fig. 11a]
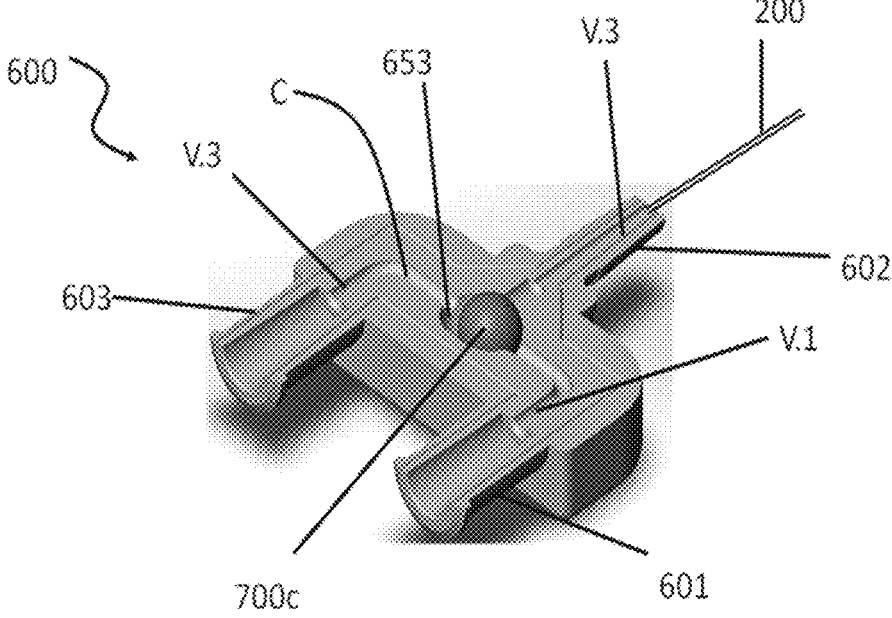
[Fig. 11b]
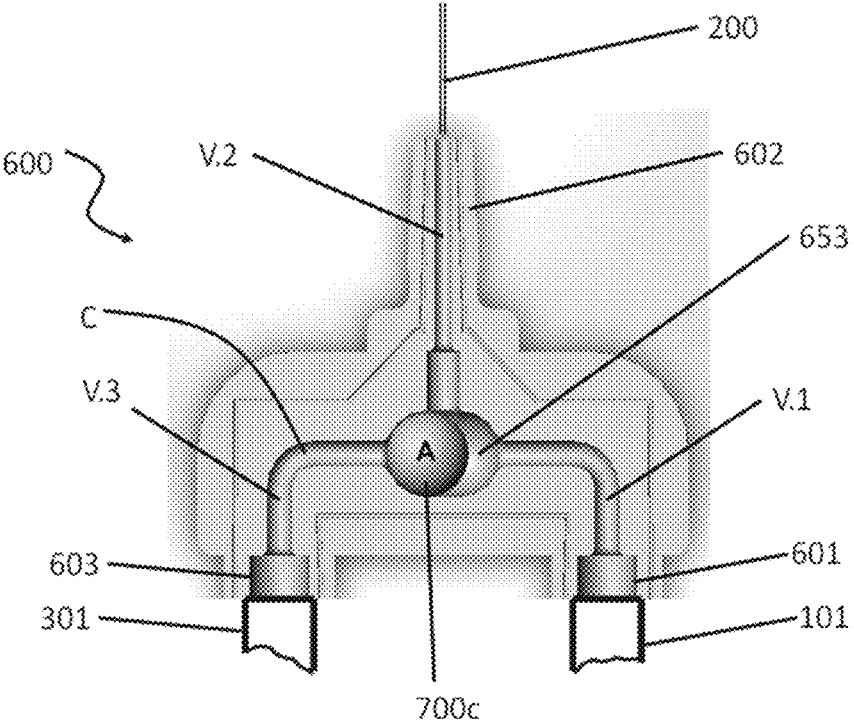

[Fig. 11c]
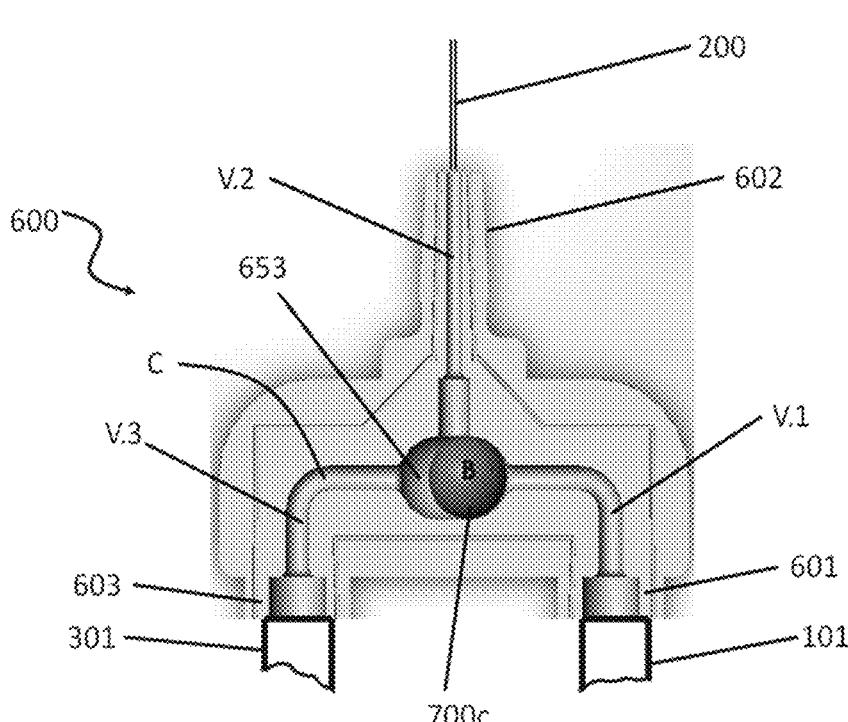

INJECTION SYRINGE

CROSS-REFERENCE TO RELATED APPLICATIONS

This application is the U.S. National Stage of PCT/FR2021/050664, filed Apr. 15, 2021, which in turn claims priority to French patent application number 2003755 filed Apr. 15, 2020. The content of these applications are incorporated herein by reference in their entireties.

TECHNICAL FIELD

The subject matter of the invention is a syringe allowing a product to be safely injected into a body injection site of an individual.

The invention relates to the technical field of injection systems and apparatuses used notably in the medical, dermatology or cosmetology fields.

PRIOR ART

In the field of dermatology or cosmetics, it is common practice to use dermal filler products. This product is administered by injection using a syringe, generally in the supraperiosteal plane, into or above the subcutaneous fat pad. These injections are among the most common minimally invasive procedures performed by dermatologists and plastic surgeons to address skin collapse and/or fill wrinkles.

The administration of the filler is sometimes complicated by adverse effects such as: swelling, necrosis or anaphylaxis. There are also important vital complications reported in the literature, such as visual impairment, skin necrosis or blindness.

The greatest danger comes from intravascular injection. The general rules for safe injections comprise aspirating blood before injection for safety reasons. In particular, air is removed from the syringe beforehand by priming (or purging) the needle with the product to be injected. When the needle is inserted into the individual's skin, the practitioner performs a plunger retraction movement to aspirate a body fluid sample (hereinafter referred to as in vivo aspiration). The practitioner then visually observes if the aspirated sample contains blood. If this is the case, the product will be injected into a blood vessel, with the risks described above. In this case, the injection site must be modified.

The aspiration of blood with the needles used for the injection of a filler (typically 29 G or 31 G gauge needles) is impractical due to the high dynamic viscosity of the fillers used. Therefore, it is common for the practitioner to simply not be able to perform the pre-aspiration of the body fluid sample and therefore not be able to check whether the needle reaches a blood vessel or not.

Further, purging the air contained in the needle, by the active product to be injected, results in partial loss of said product. However, these products are usually expensive.

The invention aims to remedy this state of affairs. More particularly, the invention aims to propose an injection syringe enabling at least one of the following objectives to be achieved:

to enable safe and reliable injections, to ensure simple and effective in vivo aspiration before the active product is injected, to reduce losses of the active product to be injected, to propose a syringe of simple design, cheap to manufacture, reliable and easy to use.

DESCRIPTION OF THE INVENTION

The solution proposed by the invention is an injection syringe for injecting a first injectable product into a body injection site of an individual, comprising:

a first syringe barrel containing the first injectable product, a first plunger being displaceably mounted in said first syringe barrel;

a hollow needle suited to being introduced into said body injection site;

an adapter connected to said first syringe barrel and to said needle.

This injection syringe is remarkable in that it further comprises a verification device making it possible to ensure that, when the first injectable product is injected, said hollow needle is not introduced into a blood vessel, said verification device comprising:

a second syringe barrel containing a second product and being connected to said adapter;

a second plunger being displaceably mounted in said second syringe barrel so as to cause a depression at the distal end of said hollow needle whereby a body fluid sample is aspirated into said second syringe barrel through said hollow needle and said adapter and mixes with the second product contained in said second syringe barrel giving a red color if said hollow needle is introduced into a blood vessel and the aspirated body fluid is blood.

Thus, the injection syringe according to the present invention offers the advantageous possibility of verifying before the injection of the first injectable product that the hollow needle is not inserted into a blood vessel (e.g. artery, vein, capillary) present in the injection site. This makes it possible to avoid the risks of accidental intravascular injection of certain injectable products such as dermal fillers, local anesthetics or other products whose intravascular injection should be avoided.

Also, the use of a syringe with two syringe barrels enables in vivo aspiration (by manipulating the second syringe barrel) to ensure that the injection of the active product will not be an intravascular injection, while allowing, with the same device, and through the same needle, the completely safe injection of the active product (by manipulating the first syringe barrel).

Other advantageous characteristics of the method that is the subject matter of the invention are listed below. Each of these characteristics may be considered alone or in combination with the remarkable characteristics defined above. Each of these characteristics contributes, where appropriate, to solving specific technical problems defined further in the description and to which the remarkable characteristics defined above do not necessarily contribute The latter may be subject, where applicable, to one or more divisional patent applications:

Advantageously, the adapter comprises:

a first inlet port in fluidic communication with the first syringe barrel, a second inlet port in fluidic communication with the second syringe barrel, an outlet port in fluidic communication with the needle, a conduit suited to placing the first inlet port, the second inlet port and the outlet port in fluidic communication, at least one shutter cooperating with the conduit, which shutter is configured to alternately allow or prevent:

fluidic communication between the first inlet port and the outlet port, and/or fluidic communication between the second inlet port and the outlet port.

According to one embodiment, the conduit comprises at least one elastically deformable wall, and the shutter is in the form of at least one pressing member suited to flattening said deformable wall so as to occlude said conduit locally.

According to one embodiment, a single pressing member is suited to flattening the deformable wall: —in a first zone to prevent fluidic communication between the first inlet port and the outlet port; and in a second zone to prevent fluidic communication between the second inlet port and the outlet port.

According to one embodiment, an actuator displaces the pressing member between the first zone and the second zone.

According to one embodiment: —a first pressing member is suited to flattening the deformable wall of the conduit in a first zone to prevent fluidic communication between the first inlet port and the outlet port; —a second pressing member is suited to flattening the deformable wall of the conduit in a second zone to prevent fluidic communication between the second inlet port and the outlet port.

According to one embodiment, the shutter is in the form of a flap movable between an open position allowing fluidic communication between the first inlet port and the outlet port and a closed position preventing fluidic communication between said first inlet port and said outlet port.

According to one embodiment, the shutter is in the form of a flap movable between an open position allowing fluidic communication between the second inlet port and the outlet port and a closed position preventing fluidic communication between said second inlet port and said outlet port.

According to one embodiment, the first plunger and the second plunger are driven by motorized drive means.

According to one embodiment, a blood detector is installed in the adapter and/or in the first syringe barrel and/or in the second syringe barrel.

According to one embodiment, the fluidic communication between the first inlet port and the outlet port is suited to allowing an injection of the first product through the needle, into the injection site, when: —the first plunger is pushed into the first syringe barrel; —and the shutter prevents fluidic communication between the second inlet port and the outlet port.

According to one embodiment, the fluidic communication between the second inlet port and the outlet port is suited to allowing an injection of the second product through the needle, when: —the second plunger is pushed into the second syringe barrel; —and the shutter prevents fluidic communication between the first inlet port and the outlet port.

According to one embodiment, the fluidic communication between the second inlet port and the outlet port is suited to allowing an aspiration of a body fluid sample at the injection site, through the needle, when: —at ambient pressure and temperature, the second product has a dynamic viscosity comprised between $10^{-3}$ $N \cdot m^{-2} \cdot s$ and $10^{-2} N \cdot m^{-2} \cdot s$; —and the second plunger is pulled into the second syringe barrel.

According to one embodiment, the fluidic communication between the second inlet port and the outlet port is suited to allowing an aspiration of a body fluid sample at the injection site, through the needle, when: —the second plunger is pulled into the second syringe barrel; —and the shutter prevents fluidic communication between the first inlet port and the outlet port.

According to one embodiment, at ambient pressure and temperature, the second product has a lower dynamic viscosity than the first product.

According to one embodiment, the first product is a dermal filler in the form of an injectable solution or a medical formulation in the form of an injectable solution.

According to one embodiment, the dermal filler comprises at least one substance selected from the group consisting of: hyaluronic acid, collagen, polylactic acid, polyacrylamide gel, calcium hydroxyapatite, calcium hydroxyapatite microspheres suspended in an aqueous gel medium, tricalcium phosphate, polymethylmethacrylate microspheres, dextran beads, dextran beads suspended in non-animal derived hylan gel, elastin peptides solubilized with bovine collagen, silicone, poly-L-lactic acid, polytetrafluoroethylene (PTFE), expanded polytetrafluoroethylene (e-PTFE), and at least one of the combinations thereof.

According to one embodiment, the dermal filler comprises one or more biologically active agents such as botulinum toxins, local anesthetics, local corticosteroids, or antibiotics, amino acids, antioxidants.

According to one embodiment, the injectable medical formulation comprises one or more biologically active agents selected from the group consisting of: botulinum toxins, local anesthetics, local corticosteroids, antibiotics, amino acids, antioxidants, opacifiers, and at least one of the combinations thereof.

According to one embodiment, the second product is a physiological liquid saline solution.

BRIEF DESCRIPTION OF THE FIGURES

Other advantages and characteristics of the invention will become clear on reading the description of a preferred embodiment which will follow, with reference to the appended drawings, made as indicative and non-limiting examples and in which:

FIG. 1 is a schematic exploded view of a syringe compliant with the invention, according to a first embodiment, FIG. 2 is a perspective view of a syringe compliant with the invention according to a second embodiment, FIG. 3 is an exploded view of the syringe of FIG. 2, FIG. 4*a* is a cross-sectional view of an adapter according to a first embodiment, the shutter being in the closed position, FIG. 4*b* shows the adapter of FIG. 4*a*, the shutter being in the open position, FIG. 5*a* schematically shows the distribution of the two products of the syringe in the adapter of FIGS. 4*a* and 4*b*, in one configuration, FIG. 5*b* schematically shows the distribution of the two products of the syringe in the adapter of FIGS. 4*a* and 4*b*, in another configuration, FIG. 5*c* schematically shows the distribution of the two products of the syringe in the adapter of FIGS. 4*a* and 4*b*, in another configuration, FIG. 5*d* schematically shows the distribution of the two products of the syringe in the adapter of FIGS. 4*a* and 4*b*, in another configuration, FIG. 6*a* schematically shows the distribution of the two products of the syringe in an adapter according to a second embodiment, in one configuration, FIG. 6b schematically shows the distribution of the two products of the syringe in the adapter of FIG. 6a, in another configuration, FIG. 7a schematically shows the distribution of the two products of the syringe in an adapter according to a third embodiment, in one configuration, FIG. 7b schematically shows the distribution of the two products of the syringe in the adapter of FIG. 7a, in another configuration, FIG. 8a schematically shows the distribution of the two products of the syringe in an adapter according to a fourth embodiment, in one configuration, FIG. 8b schematically shows the distribution of the two products of the syringe in the adapter of FIG. 8a, in another configuration, FIG. 9a schematically shows the distribution of the two products of the syringe in an adapter according to a fifth embodiment, in one configuration, FIG. 9b schematically shows the distribution of the two products of the syringe in the adapter of FIG. 9a, in another configuration, FIG. 10a shows a syringe compliant with the invention, according to a third embodiment, and according to an initial configuration of use, FIG. 10b shows the syringe of FIG. 10a, according to a second configuration of use.

FIG. 11a is a cross-sectional view in perspective of an adapter according to a sixth embodiment, the shutter being housed in a cavity arranged at the intersection between the three fluidic communication channels of the adapter, FIG. 11b schematically shows the distribution of the two products of the syringe in the adapter of FIG. 11a, in one configuration, FIG. 11c schematically shows the distribution of the two products of the syringe in the adapter of FIG. 11a, in another configuration,

DESCRIPTION OF EMBODIMENTS

For the sake of clarity, as used herein, unless otherwise specified, the use of 'first', 'second', etc. ordinal adjectives to describe an object simply indicates that different occurrences of similar objects are mentioned and does not imply that the objects thus described must be in a given sequence, whether in time, space, classification or otherwise. Similarly, the use of the adjectives "proximal/distal", "upper/lower", right/left", "forward/backward" etc. simply makes it possible to describe the position of an object in the configuration of the appended figures, but does not imply that, in practice, similar objects are in the same position.

The syringe that is the subject matter of the invention is particularly suited for the implementation of a non-therapeutic, dermatological or cosmetological treatment, comprising a prior step of in vivo aspiration and a step of injecting an active product into a body injection site of an individual, such as a dermal filler. The implementation of such a treatment is particularly effective when in vivo aspiration is carried out with a fluid less viscous than the active product injected into the injection site.

The syringe can however be used with products having similar dynamic viscosities and/or within the scope of a therapeutic treatment, notably for the safe injection of an injectable medical formulation, for example in the case of vascular surgeries, venous therapies, local pain treatment, intrathecal or epidural injections, etc.

In FIG. 1, the syringe S comprises two syringe barrels, 101 and 301 respectively. Each syringe barrel is preferably cylindrical in shape, the inner wall of which defines a chamber 102, 302 with a capacity of for example 1 mL to 20 mL. The syringe barrels 101 and 301 can be of different types and/or sizes. Each syringe barrel 101, 301 has a proximal end 105, 305 (or discharge tip) through which the product flows out of the chamber 102, 302, and a distal end 103, 303 opposite said proximal end. The syringe barrels 101, 301 may be made of plastic, steel, glass or any other material suitable for those skilled in the art.

Both syringe barrels 101, 301 may be left free (FIGS. 1, 10a, 10b) or be installed in a cover 500 that protects them (FIGS. 2 and 3). At least the part of the cover 500 in front of the syringe barrels 101, 301, is preferably made of transparent material, for example glass or plastic, such that the user can control the remaining volume of the products F1 and F2.

The first syringe barrel 101 (more particularly its chamber 102) is intended to contain a first injectable product F1 and the second syringe barrel 301 (more particularly its chamber 302) is intended to contain a second product F2. Prior to use of the syringe S, the two syringe barrels 101, 301 are pre-filled with their respective products, F1, F2, according to any appropriate method and known to those skilled in the art.

For a dermatological or cosmetic application, the first product F1 is preferentially a dermal filler in the form of an injectable solution (liquid, gel, suspended particles). This product F1 comprises at least one substance selected from the group consisting of: hyaluronic acid, collagen, polylactic acid, polyacrylamide gel, calcium hydroxyapatite, calcium hydroxyapatite microspheres suspended in an aqueous gel carrier, tricalcium phosphate, polymethylmethacrylate microspheres, dextran beads, dextran beads suspended in non-animal hylan gel, elastin peptides solubilized with bovine collagen, silicone, poly-L-lactic acid, polytetrafluoroethylene (PTFE), expanded polytetrafluoroethylene (e-PTFE) and at least one of the combinations thereof. It may also comprise one or more biologically active agents such as botulinum toxins, local anesthetics, local corticosteroids, or antibiotics, amino acids, antioxidants.

For a therapeutic application, the first product F1 may be a medical formulation in the form of an injectable liquid solution (liquid, suspended particles). This injectable medical formulation comprises one or more biologically active agents selected from the group consisting of: botulinum toxins, local anesthetics, local corticosteroids, antibiotics, amino acids, antioxidants, opacifiers, and at least one of the combinations thereof.

The second product F2 is preferably a neutral injectable product (i.e. without known effect on the individual from a dermatological, cosmetic, or therapeutic point of view), notably a physiological liquid saline solution, for example a solution composed of distilled water and sodium chloride (NaCl) diluted from 1/1000 to 10/1000.

According to a preferred embodiment, the two products F1 and F2 do not have the same dynamic viscosity. In particular, the second product F2 is less viscous than the first active product F1. For example, at ambient temperature and pressure, the first product F1 may have a dynamic viscosity between 0.1 Pa·s and 1000 Pa·s (N·m$^{-2}$·s) and the second product F2 may have a dynamic viscosity between $10^{-3}$ Pa·s and $10^{-2}$ Pa·s. The use of a second low viscosity product F2 allows the in vivo aspiration step to be carried out in a very simple manner, without any particular resistance.

In the following description, and for the sake of clarity and conciseness only, the first product F1 will be called the filling fluid and the second product F2 will be called the saline solution The saline solution has a lower dynamic viscosity than the filling fluid.

Conventionally, a first plunger 110 is displaceably mounted in the first body 101 and a second plunger is displaceably mounted in the second body 301. Each plunger 110, 310 is inserted from the distal end 103, 303 of the respective syringe barrel 101, 301 and is translationally moveably mounted in said barrel. When a plunger 110, 310 is pushed forward, that is to say when it is moved towards the proximal end 105, 305 of the syringe barrel 101, 301, the volume of the chamber 102, 302 decreases and the pressure inside the syringe barrel increases. The product F1, F2 can then be evacuated out of the syringe barrel, through its proximal end 105, 305. Conversely, when a plunger 110, 310 is pulled back—or retracted, that is to say displaced to the distal end 103, 303 of the syringe barrel 101, 301, the volume of the chamber 102, 302 increases and the pressure inside said syringe barrel decreases. This depressurization allows a fluid to be aspirated from the proximal end 105, 305.

The plungers 110, 310, are made of plastic or metal. They are advantageously provided with seals on their outer wall. They are suited to their respective syringe barrels and can be of different types and/or sizes.

The second plunger 310 can be operated independently of the first plunger 110. In other words, both plungers can be manipulated independently of each other. Each product F1 or F2 can therefore be injected independently and/or the volume of the chambers 102, 302 can be varied in an independent manner, in order to independently increase or decrease the pressure in each barrel 101, 301.

In the embodiment of FIGS. 1, 10a and 10b, the plungers 110, 310 are manually maneuverable. They are each connected to a rod 111, 311 (made of plastic or steel) each extending from a pusher 112, 312. By manually pulling or pushing the pusher 112, 312 with his fingers, the practitioner can displace the corresponding plunger 110, 310 inside the syringe barrel 101, 301.

In the embodiment of FIGS. 2 and 3, the plungers 110, 310 are driven by motorized drive means 410, 430, for example of the worm or rack type rotated by one or more electric rotary motors optionally associated with one or more drive pinions. The drive means 410, 430 are installed in a protective frame 400 that also incorporates an electric battery 420 (battery or rechargeable battery type) and an electronic management unit 440. Control buttons 411, 431, or other dedicated buttons, are mounted on the outer wall of the frame 400 so that they can be selected by the user to control the movement of the plungers 110, 310.

Compared to the embodiment of FIGS. 1, 10a and 10b, this motorized mode of actuation allows each of the plungers 110, 310 to be moved more precisely and thus to optimally dispense the product F1 and/or product F2. The plungers 110, 310 can be driven continuously or intermittently as required.

The frame 400 is advantageously integral with the cover 500 so that the assembly forms a one-piece apparatus, particularly ergonomic and easy for the user to handle. The frame 400 may further comprise a syringe power button (on/off button) and, if applicable, appropriate display means that indicate the charge level of the electric battery 420 and/or the fill level of the syringe barrels 101, 103.

According to one embodiment, the electronic management unit 440 is programmed to automatically displace the plungers 110, 310, synchronously or sequentially, according to predefined cycles. For example, the sequential execution of the in vivo purge and/or aspiration phases described earlier in the description can be pre-programed. The same applies to the sequenced activation of the shutter(s) described earlier in the description.

The syringe S also comprises a hollow needle 200 which is unique and common to each of the syringe barrels 101, 301. The needle 200 is preferentially a conventional hypodermic needle, but may be a micro-cannula. As an example, the needle 200 has a caliber—or gauge—ranging from 18 G to 34 G, more particularly from 25 G to 30 G. For example, its length is between 0.5 cm and 4 cm. The distal end 202 of the needle 200 is of beveled shape, as known by the those skilled in the art, in order to facilitate its insertion into the injection site. A needle holder 203 is advantageously mounted on the proximal end of the needle 200. The user can thus easily change the needle.

An adapter 600 is connected to the first syringe barrel 101, to the second syringe barrel 301 and to the needle 200. This adapter 600 may be made of plastic material, notably plastics compatible with non-therapeutic and therapeutic applications of the invention such as Acrylonitrile Butadiene Styrene (ABS); nylon; Polycarbonate (PC); Polypropylene (PP); Poly(vinyl chloride) (PVC). The adapter 600 can further be made of stainless steel, steel, etc. It comprises a first inlet port 601 in fluidic communication with the first syringe barrel 101, a second inlet port 603 in fluidic communication with the second syringe barrel 301, and an outlet port 602 in fluidic communication with the needle 200. For example, the adapter 600 can be contained in an envelope of dimensions 30 mm×35 mm×10 mm.

In FIG. 1, the first inlet port 601 is dismountably connected to the proximal end 105 of the first syringe barrel 101. The connection may comprise a locking device of Luer-Lock type. The connection of the second inlet port 601 to the proximal end 305 of the second syringe barrel 301 is similar. In FIGS. 2 and 3, the inlet ports 601, 603 are sealingy engaged with the proximal ends 105, 305. In FIGS. 1 to 3, the outlet port 602 is dismountably connected to the needle holder 203, for example by means of a locking device of Luer-Lock type.

In FIG. 4a, the adapter 600 has an internal conduit C suited to placing the first inlet port 601, the second inlet port 603 and the outlet port 605 in fluidic communication. As an example, the conduit C has a circular cross-section, the internal diameter of which is comprised between 0.1 mm and 10 mm. In practice, the cross-section and/or internal diameter of the conduit C is chosen as a function of the type of product to be injected and/or its injection dose. In the appended figures, the conduit C has a T or Y shape, the main branch of which emerges at the outlet port 602 and of which each side branch emerges at an inlet port 601, 603 respectively.

The adapter 600 comprises at least one shutter cooperating with the conduit C. This shutter is configured to alternately allow or prevent: fluidic communication between the first inlet port 601 and the outlet port 602, and/or fluidic communication between the second inlet port 603 and the outlet port 602. By specifically actuating this shutter, the user can easily seal a portion of the conduit C to isolate one or the other of the syringe barrels 101, 301 and control the product to be passed through the needle 200.

Different embodiments of this shutter will now be described with reference to the different appended figures. Different sequences of use of the syringe S are also described with reference to these figures.

First Embodiment: FIGS. 4a to 5d

The adapter 600 comprises a single shutter 70 movable between an open position (FIG. 4a) allowing fluidic communication between the second inlet port 603 and the outlet port 602 and a closed position (FIG. 4*b*) preventing fluidic communication between said second inlet port and said outlet port. This shutter 70 is arranged at the second inlet port 603, in the branch of the conduit C associated with said second port. The other branch of the conduit C associated with the first inlet port 601 is free, that is to say without a shutter or other member performing this function.

This shutter 70 is in the form of a flap cooperating with a flap seat installed in the conduit C. When the flap bears against its seat, the conduit C is sealingly closed. And when the flap is at a distance from its seat, the product can flow freely into the conduit C. This flap may be a non-return flap allowing the product to flow in one direction only to prevent mixing of the products F1, F2. According to another embodiment, the flap 70 is integrated in a valve or a solenoid valve installed in the conduit C.

According to one embodiment, the flap 70 is manually activated, for example by means of a push button or a knob, suited to switching it between the open and closed positions. In the embodiment of FIGS. 10*a* and 10*b*, the second syringe barrel 301 is pivotally mounted on the adapter 600, around an axis A perpendicular to the axis of said barrel. In the position of FIG. 10*a*, the flap 70 is in the open position. By rotating the second syringe barrel 301 around the axis A, for example in a clockwise direction which moves it away from the first syringe barrel 101, the flap 70 is in the closed position (FIG. 10*b*). The user must thus flip the second syringe barrel 301 around the axis A to open or close the flap 70.

According to another embodiment, the flap 70 is integrated in the locking device of Luer-Lock type allowing the proximal end 305 of the second syringe barrel 301 to be connected to the second inlet port 603. By rotating this device in one direction, for example ¼ turn or ½ turn clockwise, the flap 70 is placed in the open position. And by rotating this device in the other direction, for example ¼ turn or ½ turn anti-clockwise, the flap 70 is placed in the closed position.

According to another embodiment, the flap 70 is displaced by means of an electromechanical actuator which, for example, may be in the form of an electric motor or an electromagnet, the power supply of which is controlled by the electronic management unit 440. In this case, switching the flap 70 between the open and closed positions can be controlled by activating a dedicated control button 450 installed on the frame 400 (FIGS. 2 and 3). The flap 70 may further be maneuvered by means of a hydraulic or pneumatic actuator in the form of, for example, a jack, the rod of which is connected to said flap.

According to another embodiment, the flap 70 is an element of a microfluidic valve suited to being displaced under the effect of pressure. For example, when the second plunger 310 is pushed forward, the pressure inside the second barrel 301 increases, which tends to circulate the saline solution F2 out of said barrel, to penetrate into the conduit C. The saline solution F2 then exerts a pushing pressure on the flap 70 which tends to open it, such that said saline solution can flow from the second inlet port 603 to the outlet port 602. The use of a microfluidic valve allows the flap 70 to be made passive, i.e. it does not require an actuator to operate it The sequence of use of the syringe S equipped with the adapter 600 in FIGS. 4*a* and 4*b* will now be described with reference to FIGS. 5*a* to 5*d*.

FIG. 5*a*. The syringe S is in an initial state: the flap 70 is in the closed position and the two plungers 110, 310 are at rest.

FIG. 5*b*. To purge the air in the needle 200, the flap 70 is placed in the open position, and the second plunger 310 is pushed forward. The saline solution F2 then flows from the second inlet port 603 to the outlet port 602 so as to purge the air contained in the needle. This pre-purge is therefore carried out with a particularly inexpensive neutral liquid, and in any case is not carried out with the filling fluid F1. After purging, the needle 200 is then inserted into the injection site.

In vivo aspiration may be performed easily in the configuration shown in FIG. 5*b*. The second plunger 310 is pulled back to create a depression in the channel C at the second inlet port 603. The saline solution F2 contained in the conduit C and the needle 200 then flows back from the outlet port 602 to the second inlet port 603, while causing a body fluid sample to be aspirated. This body fluid is aspirated without risk of mixing with the filler fluid F1. In other words, the filler fluid F1 is not soiled by the aspirated body fluid.

However, this in vivo aspiration may also be performed, with more force however and with a risk of fouling the filler fluid F1, by closing the flap 70 and by pulling backwards the first plunger 110 so as to create a depression in the conduit C, at the first inlet port 601.

In both cases, since the saline solution F2 has a low dynamic viscosity, this in vivo aspiration is carried out without any difficulty, the resistance to pulling the plunger back being very low, even with a small diameter needle (e.g. 18 G to 34 G needle). The user can then verify that no blood has entered the syringe barrel through which the aspiration is performed. This verification can be visual, the user sees a reddish coloration of the saline solution (respectively the filling fluid), if blood is aspirated into the second syringe barrel 301 (respectively into the first syringe barrel 101). This can also be done automatically, for example by integrating a blood detector 610 into the syringe S. This detector 610 is preferably connected to the electronic management unit 440 (FIGS. 3 and 4). It is preferably installed in the adapter 600 (FIGS. 4*a*-5*d*) and/or in the first syringe barrel 101 and/or in the second syringe barrel 301. This detector 610 may be based on detection of a blood component, for example glucose detection. When glucose is detected in the syringe S (in the adapter 600 and/or in one of the syringe barrels 101, 301), then the electronic management unit 440 can emit a visual and/or audible signal to the user that the needle 200 is inserted into a blood vessel.

FIG. 5*c*. The user having ensured himself that the needle 200 is not inserted into a blood vessel, he can perform the injection of the filling fluid F1. To do this, the flap 70 is placed in the closed position and the first plunger 110 is pushed forward. The filling fluid F1 then flows from the first inlet port 601 to the outlet port 602, to be injected from the needle 200.

FIG. 5*d*. In practice, the filler F1 is injected into several injection sites of the individual. Between two injections, the user purges the needle 200 of filler fluid F1 so that he can once again carry out in vivo aspiration. To do this, the flap 70 is placed in the open position, and the second plunger 310 is pushed forward. With the needle 200 open at its distal end, the resistance of the filler fluid F1 present in the needle 200 is lower than that of the filler fluid F1 present in the conduit C, in the portion situated between the outlet port 602 and the first inlet port 601. Also, by pushing the second plunger 310 forward, the saline solution F2 will flow into the needle 200 and purge it of filling fluid F1. Only a very small volume of filler fluid F1 is thus lost. After this purging, a configuration similar to that of FIG. 5b is then found, allowing safe in vivo aspiration.

Second Embodiment: FIGS. 6a and 6b

The fan 70 is arranged at the first inlet port 601, in the branch of the conduit C associated with said first port. The other branch of the conduit C associated with the second inlet port 603 is free. This flap 70 and its mode of actuation are similar to those described above.

FIG. 6a. To purge the air in the needle 200, the flap 70 is maintained in the closed position, and the second plunger 310 is pushed forward so that the saline solution F2 flows into the needle 200 and purges it of air.

In vivo aspiration is carried out in the same way as described with reference to FIG. 5b. The flap 70 remains closed and the second plunger 310 is pulled back so as to cause an aspiration of a body fluid sample through the needle 200. This in vivo aspiration may also be carried out by keeping the flap 70 open and by pulling back the first plunger 110 to create a depression in the conduit C, at the first inlet port 601.

FIG. 6b. The injection of the filler fluid F1 into the injection site is carried out by placing the flap 70 in the open position and by pushing the first plunger 110 forward.

To purge the needle 200 of filler fluid F1 between two injections, the flap 70 is placed in the closed position, and the second plunger 310 is pushed forward. As explained with reference to FIG. 5d, the saline solution F2 flows into the needle 200 and purges it of filling fluid F1.

Third Embodiment: FIGS. 7a and 7b

The adapter 600 comprises two flaps 70a, 70b. The first flap 70a is arranged at the first inlet port 601, in the branch of the conduit C associated with said first port. The second flap 70b is arranged at the second inlet port 603, in the branch of the conduit C associated with said second port. Each of these flaps 70a, 70b and their mode of actuation are similar to those described above. They can also be in the form of a non-return flap.

FIG. 7a. To purge the air in the needle 200, the first flap 70a is closed and the second flap 70a is opened. By pushing the second plunger 310 forward, the saline solution F2 flows into the needle 200 and purges it of air.

In vivo aspiration is carried out in the same way as described with reference to FIG. 5b. The first flap 70a remains closed and the second flap 70b remains open. The second plunger 310 is pulled back so as to cause an aspiration of a body fluid sample through the needle 200. This in vivo aspiration may also be carried out by maintaining the first flap 70a open, by closing the second flap 70b and by pulling the first plunger 110 backward so as to create a depression in the conduit C, at the first inlet port 601.

FIG. 7b. The injection of the filler fluid F1 into the injection site is achieved by opening the first flap 70a, closing the second flap 70b and pushing the first plunger 110 forward.

To purge the needle 200 of filler fluid F1 between two injections, the first flap 70a is closed, the second flap 70b is opened, and the second plunger 310 is pushed forward. As explained with reference to FIG. 5d, the saline solution F2 flows into the needle 200 and purges it of filling fluid F1.

Fourth Embodiment: FIGS. 8a and 8b

The conduit C has at least one elastically deformable wall P. This wall P is made of an elastically deformable plastic material such as a flexible thermoplastic based on PVC, FEP (Fluorinated Ethylene Propylene), PTFE (polytetrafluoro-ethylene) silicone, or a rubber. To simplify the design, the whole of the conduit C is made of such an elastically deformable material.

In the same way as a peristaltic pump, a pressing member 700 makes it possible to flatten the deformable wall P so as to locally occlude the conduit C. It flattens out locally and then returns to its original shape, due to its elasticity. According to one embodiment, the pressing member 700 is in the form of a wheel or a roller.

The pressing member 700 flattens the deformable wall P into two separate zones: a first zone (FIG. 8a) to prevent fluidic communication between the first inlet port 601 and the outlet port 602; and a second zone (FIG. 8b) to prevent fluidic communication between the second inlet port 603 and the outlet port 602. The first zone is situated on the side of the first inlet port 601, in the branch of the conduit C associated with said first port. Conversely, the second zone is situated on the side of the second inlet port 601, in the branch of the conduit C associated with said second port.

The pressing member 700 is connected to a suitable actuator 710 to displace it between the two flattening zones. According to one embodiment, the actuator 710 is a mechanical actuator, for example connected to a manually operated push button or knob, suited to displacing the pressing member 700 between the different flattening zones. According to an alternative embodiment, the mechanical actuator 710 (and/or the pressing member 700) cooperates with the locking devices of Luer-Lock type enabling the proximal ends 105, 305 to be connected to the inlet ports 601, 603. By rotating the locking device associated with the first syringe barrel 101 in one direction, e.g. ¼ turn or ½ turn clockwise, the pressing member 700 acts in the first zone. And by rotating this device in the other direction, for example ¼ turn or ½ turn anti-clockwise, the pressing member 700 acts in the second zone. It can also be provided that, by pivoting the locking device associated with the second syringe barrel 301, that the pressing member 700 is displaced to the second zone.

According to another embodiment, the pressing member 700 is displaced by means of an electromechanical actuator 710. This can be in the form of an electric motor or an electromagnet, the power supply of which is controlled by the electronic management unit 440. In this case, the displacement of the pressing member 700 between the two flattening zones may be controlled by the activation of a dedicated control button 450 installed on the frame 400 (FIGS. 2 and 3). The actuator 710 may also be in the form a hydraulic or pneumatic actuator and may for example be in the form of a jack, the rod of which is connected to the pressing member 700.

FIG. 8a. To purge the air in the needle 200, the pressing member 700 is placed so that it acts in the first flattening zone. By pushing the second plunger 310 forward, the saline solution F2 flows into the needle 200 and purges it of air.

In vivo aspiration is carried out in the same way as described with reference to FIG. 5b. The pressing member 700 remains active in the first flattening zone. The second plunger 310 is pulled back so as to cause an aspiration of a body fluid sample through the needle 200. This in vivo aspiration may also be achieved by displacing the pressing member 700 so that it acts in the second flattening zone and by pulling the first plunger 110 backwards so as to create a depression in the conduit C at the first inlet port 601.

FIG. 8b. The injection of the filler fluid F1 into the injection site is performed by maneuvering the pressing member 700 so that it acts in the second flattening zone and by pushing the first plunger 110 forward.

To purge the needle 200 of filler fluid F1 between two injections, the pressing member 700 is again placed so that it acts in the first flattening zone (FIG. 8*a*), and the second plunger 310 is pushed forward. As explained with reference to FIG. 5*d*, the saline solution F2 flows into the needle 200 and purges it of filling fluid F1.

Fifth Embodiment: FIGS. 9a and 9b

This embodiment is similar to the fourth embodiment described previously. However, two pressing members 700*a*, 700*b* are used. A first pressing member 700*a* is suited to flattening the deformable wall P of the conduit C in the first zone (FIG. 9*a*) in order to prevent fluidic communication between the first inlet port 601 and the outlet port 602. The second pressing member 700*b* is suited to flattening the deformable wall P of the conduit in the second zone (FIG. 9*b*) in order to prevent fluidic communication between the second inlet port 603 and the outlet port 602.

Each of these pressing members 700*a*, 700*b* and their mode of actuation are similar to those described above. The actuators 700*a*, 700*b* may however be configured to simply perform a forward/backward translation movement. In the forward position, the pressing member 700*a*, 700*b* flattens the deformable wall P, and in the set back position, it allows said wall to return to its original shape. In the following description, and for the sake of brevity, a pressing member is said to be "active" or "activated" when it flattens the deformable wall P, and "inactive" or "inactivated" otherwise.

FIG. 9*a*. To purge the air in the needle 200, the first pressing member 700*a* is active in the first flattening zone, the second pressing member 700*b* is inactive in the second flattening zone. By pushing the second plunger 310 forward, the saline solution F2 flows into the needle 200 and purges it of air.

In vivo aspiration is carried out in the same way as described with reference to FIG. 5*b*. The first pressing member 700*a* remains active and the second pressing member 700*b* inactive. The second plunger 310 is pulled back so as to cause an aspiration of a body fluid sample through the needle 200. This in vivo aspiration may also be achieved by activating the second pressing member 700*b*, by inactivating the first pressing member 700*a* and by pulling the first plunger 110 backwards in order to create a depression in the conduit C at the first inlet port 601.

FIG. 9*b*. The injection of the filling fluid F1 into the injection site is carried out by inactivating the first pressing member 700*a*, by activating the second pressing member 700*b* and by pushing the first plunger 110 forward.

To purge the needle 200 of filling fluid F1 between two injections, the first pressing body 700*a* is activated, the second pressing body 700*b* is deactivated (FIG. 9*a*), and the second plunger 310 is pushed forward. As explained with reference to FIG. 5*d*, the saline solution F2 flows into the needle 200 and purges it of filling fluid F1.

Sixth Embodiment: FIGS. 11a to 11c

The adapter 600 comprises a cavity 653 arranged at the intersection between the three fluidic communication channels (or branches) V.1, V.2, V.3 of the conduit C.

The cavity 653 has a first orifice connected to the channel V.1 of the conduit C associated with the first inlet port 601, a second orifice connected to the channel V.3 of the conduit C associated with the first inlet port 601, and a third orifice connected to the channel V.2 of the conduit C associated with the outlet port 602.

The cavity 653 houses a shutter 700*c*. This is in the form of a movable element slidingly mounted inside the cavity 653 between a first position in which it occludes fluidic communication between the second inlet port 603 and the outlet port 602 when the first injectable product F1 is discharged out of the first syringe barrel 101 for the purpose of injecting the first injectable product F1 into the body injection site (FIG. 11*b*), and a second position in which it occludes fluidic communication between the first inlet port 601 and the outlet port 602 when aspirating the body fluid sample into the second syringe barrel 301 (FIG. 11*c*).

The cross-section of the cavity 653 corresponds to the cross-section of the movable part so that it can slide in the cavity 653.

According to one embodiment, the cavity 653 has a general tubular shape of substantially circular or oblong cross-section and the movable element representing the shutter 700*c* has a cross-sectional shape corresponding substantially to the cross-section of the cavity 653 (for example, in the shape of a sphere or ball for a cavity 653 of circular cross-section).

The movable element representing the shutter 700*c* may be made of plastic, stainless steel, glass, ceramic or any other material suitable for those skilled in the art.

FIG. 11*b*. To inject the first injectable F1 into the injection site, the first plunger 101 is pushed forward. The injectable product F1 coming out of the first syringe barrel 101 enters the cavity 653 via the first orifice connected to the channel V.1 of the conduit C and pushes the shutter 700*c* (or movable element), into the cavity 653, in the direction of the second orifice that is connected to the channel V.3 of the conduit C in order to occlude fluidic communication between the second inlet port 603 and the outlet port 602. Fluidic communication between the first inlet port 601 and the outlet port 602 is then allowed to enable the first injectable product F1 to be injected into the injection site.

FIG. 11*c*. To carry out in vivo aspiration of the body fluid sample from the injection site, the first plunger 110 is pulled backwards to create a depression in the channel V.1 of the conduit C whereby the shutter 700*c* (or movable element) is aspirated, inside the cavity 653, in the direction of the first orifice connected to the channel V.1 in order to occlude the fluidic communication between the first inlet port 601 and the outlet port 602. Fluidic communication between the second inlet port 603 and the outlet port 602 is then allowed to enable the aspiration of the body sample from the injection site, into said second syringe barrel 301 through the hollow needle 200 and the adapter 600. Next, the second plunger 310 is pulled back so as to create a depression at the distal end of the hollow needle (200) under the effect of which the body fluid sample is aspirated into the second syringe barrel 301 through the hollow needle 200 and adapter 600 (channels V2+V3). Thus, the body fluid sample can be aspirated without risk of mixing with the first injectable fluid F1 (e.g. filler).

To summarize, by manipulating the shutter 70, 70*a*, 70*b*, 700, 700*a*, 700*b*, 700*c*, the user can easily isolate one or the other of the syringe barrels, to control the product to be passed through the single needle. Notably, the needle can be purged with a particularly inexpensive, neutral product contained in the second syringe barrel. The active product is only used for the treatment of the individual, so its use is optimized in terms of quantity.

The arrangement of the different elements and/or means and/or steps of the invention, in the embodiments described above, should not be understood as requiring such arrangement in all implementations. Other alternatives may be provided, including:

The syringe may comprise more than two syringe barrels, for example three or four, each containing a separate product. The adapter 600 then has other inlet ports enabling their connection.

The inlet ports 601, 603 may be non-removeably attached to the syringe barrels 101, 301, for example by molding, gluing or welding.

The needle 200 may be non-removeably installed on the adapter 600.

The first product F1 may be in the form of a powder (e.g. intended to be mixed with the second product F2 in the adapter) or in the form of a gas (e.g. a gas for medical use such as ozone). The same applies to the second product F2.

The second product F2 may consist of an injectable dermal filler (liquid or gel), an injectable medical formulation, etc. the injection of three fluids or four fluids for example.

The drive means 410, 430 may be in the form of pneumatic or hydraulic actuators (for example of jack type), or electromagnetic actuators (for example of electromagnet type).

In an application where the active product F1 must be injected into the blood stream (intravenous injection), the in vivo aspiration step may be performed to ensure that the aspirated body fluid sample is indeed blood.

The adapter 600 may comprise a flap 70 in a branch of the conduit C and a pressing member 700 in the other branch.

Further, one or more characteristics only described in one embodiment may be combined with one or more other characteristics only described in another embodiment. Similarly, one or more characteristics only described in one embodiment may be generalized to the other embodiments.

The invention claimed is:

1. An injection syringe for injecting a first injectable product into a body injection site of an individual, comprising:

a first syringe barrel containing the first injectable product, a first plunger being displaceably mounted in said first syringe barrel;

a hollow needle adapted to being inserted into said body injection site;

an adapter connected to said first syringe barrel and said needle, and a verification device configured to ensure that, when the first injectable product is injected, said hollow needle is not introduced into a blood vessel, said verification device comprising:

a second syringe barrel containing a second product and being connected to said adapter;

a second plunger being displaceably mounted in said second syringe barrel so as to cause a depression at a distal end of said hollow needle whereby a sample of body fluid is aspirated into said second syringe barrel through said hollow needle and said adapter and is mixed with the second product contained in said second syringe barrel giving a red color if said hollow needle is inserted into a blood vessel and the aspirated fluid is blood,

wherein the adapter comprises:

a first inlet port in fluidic communication with the first syringe barrel, a second inlet port in fluidic communication with the second syringe barrel, an outlet port in fluidic communication with the needle, a conduit suitable for placing the first inlet port, the second inlet port and the outlet port in fluidic communication, and at least one shutter cooperating with the conduit, which shutter is configured to alternately allow or prevent: fluidic communication between the first inlet port and the outlet port, and/or fluidic communication between the second inlet port and the outlet port, wherein the conduit comprises a cavity, a first fluid communication pathway connecting the first inlet port to the cavity through a first orifice, a second fluid communication pathway connecting the outlet port to the cavity through a second orifice, and a third fluid communication pathway connecting the second inlet port to the cavity through a third orifice, wherein the cavity is arranged at an intersection between the first, second and third fluid communication pathways of the conduit, the shutter being in the form of a movable element slidingly mounted within said cavity between a first position at which the movable element occludes the fluidic communication between the second inlet port and the outlet port upon discharge of the first injectable product out of the first syringe barrel for the purpose of injecting the first injectable product into the body injection site, and a second position at which the movable element occludes the fluidic communication between the first inlet port and the outlet port when aspirating the fluid sample into the second syringe barrel, the cavity having a general tubular shape of substantially circular or oblong cross-section and the movable element representing the shutter having a cross-sectional shape corresponding substantially to the cross-section of the cavity, and wherein, when the first plunger is pulled backwards to create a depression in the first fluid communication pathway of the conduit, the shutter is aspirated, inside the cavity, in the direction of the first orifice in order to occlude the fluidic communication between the first inlet port and the outlet port and to allow fluidic communication between the second inlet port and the outlet port to enable the aspiration of a body sample from the injection site, into said second syringe barrel through the hollow needle and the adapter such that the body fluid sample is aspirated into the second syringe barrel through the hollow needle and the second communication pathway and the third communication pathway under the effect of a depression created at the distal end of the hollow needle when the second plunger is pulled back.

2. The injection according to claim 1, wherein the first plunger and the second plunger are driven by motorized drive means.

3. The injection according to claim 1, wherein a blood detector is installed in the adapter and/or in the first syringe barrel and/or in the second syringe barrel.

4. The injection according to claim 1, wherein the second syringe barrel contains the second product, and wherein the fluidic communication between the second inlet port and the outlet port allows aspiration of a body fluid sample at the injection site, through the needle, when:

at ambient pressure and temperature, the second product has a dynamic viscosity of between $10^{-3}$ N·m$^{-2}$·s and $10^{-2}$ N·m$^{-2}$·s, and the second plunger is pulled into the second syringe barrel.

5. The injection according to claim 1, wherein the first syringe barrel contains the first injectable product and the second syringe barrel contains the second product, and wherein at ambient pressure and temperature, the second product has a lower viscosity than the first product.

6. The injection according to claim 1, wherein the first syringe barrel contains the first injectable product and the second syringe barrel contains the second product, and wherein the first product is a dermal filler in the form of an injectable solution or a medical formulation in the form of an injectable solution.

7. The injection according to claim 6, wherein the dermal filler comprises at least one substance selected from the group consisting of: hyaluronic acid, collagen, polylactic acid, polyacrylamide gel, calcium hydroxyapatite, calcium hydroxyapatite microspheres suspended in an aqueous gel carrier, tricalcium phosphate, polymethylmethacrylate microspheres, dextran beads, dextran beads suspended in hylan gel of non-animal origin, elastin peptides solubilized with bovine collagen, silicone, poly-L-lactic acid, polytetrafluoroethylene, expanded polytetrafluoroethylene, and any combination thereof.

8. The injection according to claim 6, wherein the dermal filler comprises one or more biologically active agents.

9. The injection according to claim 8, wherein the or more biologically active agents are selected from the group consisting of botulinum toxins, local anesthetics, local corticosteroids, or antibiotics, amino acids, and antioxidants.

10. The injection according to claim 6, wherein the medical formulation comprises one or more biologically active agents selected from the group consisting of: botulinum toxins, local anesthetics, local corticosteroids, antibiotics, amino acids, antioxidants, opacifiers, and any combination thereof.

11. The injection according to claim 1, wherein the second syringe barrel contains the second product, and wherein the second product is a physiological liquid saline solution.

\* \* \* \* \*